(12) United States Patent
Oshimura et al.

(10) Patent No.: US 9,420,769 B2
(45) Date of Patent: Aug. 23, 2016

(54) CHIMERIC NON-HUMAN ANIMAL CARRYING HUMAN HEPATOCYTE

(71) Applicants: Mitsuo Oshimura, Tottori (JP); Yasuhiro Kazuki, Tottori (JP); Chise Mukaidani, Higashihiroshima (JP); Takashi Shimada, Higashihiroshima (JP); Masakazu Kakuni, Higashihiroshima (JP); Satoko Hamamura, Higashihiroshima (JP); Hidetaka Kamimura, Chuo-ku (JP); Akio Kawamura, Chuo-ku (JP); Naoyuki Nakada, Chuo-ku (JP); Masato Ohbuchi, Chuo-ku (JP); Kota Kato, Chuo-ku (JP)

(72) Inventors: Mitsuo Oshimura, Tottori (JP); Yasuhiro Kazuki, Tottori (JP); Chise Mukaidani, Higashihiroshima (JP); Takashi Shimada, Higashihiroshima (JP); Masakazu Kakuni, Higashihiroshima (JP); Satoko Hamamura, Higashihiroshima (JP); Hidetaka Kamimura, Chuo-ku (JP); Akio Kawamura, Chuo-ku (JP); Naoyuki Nakada, Chuo-ku (JP); Masato Ohbuchi, Chuo-ku (JP); Kota Kato, Chuo-ku (JP)

(73) Assignees: PHOENIXBIO CO., LTD., Higashihiroshima-shi (JP); NATIONAL UNIVERSITY CORPORATION TOTTORI UNIVERSITY, Tottori-shi (JP)

( * ) Notice: Subject to any disclaimer, the term of this patent is extended or adjusted under 35 U.S.C. 154(b) by 20 days.

(21) Appl. No.: 14/351,481

(22) PCT Filed: Oct. 12, 2012

(86) PCT No.: PCT/JP2012/077019
§ 371 (c)(1),
(2) Date: Apr. 11, 2014

(87) PCT Pub. No.: WO2013/054949
PCT Pub. Date: Apr. 18, 2013

(65) Prior Publication Data
US 2014/0241991 A1    Aug. 28, 2014

(30) Foreign Application Priority Data
Oct. 13, 2011  (JP) .................. 2011-226233

(51) Int. Cl.
*A01K 67/027*  (2006.01)
*C12N 9/02*  (2006.01)
*G01N 33/50*  (2006.01)

(52) U.S. Cl.
CPC .......... *A01K 67/0271* (2013.01); *C12N 9/0042* (2013.01); *G01N 33/5067* (2013.01); *G01N 33/5088* (2013.01); *A01K 2207/12* (2013.01); *A01K 2217/075* (2013.01); *A01K 2227/105* (2013.01); *A01K 2267/03* (2013.01)

(58) Field of Classification Search
None
See application file for complete search history.

(56) References Cited

U.S. PATENT DOCUMENTS 6,509,514 B1    1/2003   Kneteman et al.
2011/0023138 A1  1/2011   Oshimura et al.

FOREIGN PATENT DOCUMENTS

| JP | 2002 45087 | 2/2002 |
| JP | 2003 526348 | 9/2003 |
| WO | 01 11951 | 2/2001 |
| WO | WO 2009050484 A1 * | 4/2009 |
| WO | WO 2009/063722 A1 | 5/2009 |

OTHER PUBLICATIONS

Hammer et al, J Anim Sci 1986;63:269-78.*
Mullins et al.J Clin Invest Apr. 1996;97:1557-60.*
Wall et al. J Dairy Sci 1997;80:2213-24.*
Pearson, Nature 2002;415:8-9.*
Nelson, D.R., et al. "P450 superfamily: update on new sequences, gene mapping, accession numbers and nomenclature" Pharmacogenetics, vol. 6, pp. 1-42, 1996.
Rhim, J. et al. "Complete reconstitution of mouse liver with xenogeneic hepatocytes" Proc. Natl. Acad. Sci. USA, vol. 92, pp. 4942-4946, May 1995.
Dandri, M. et al. "Woodchuck Hepatocytes Remain Permissive for Hepadnavirus Infection and Mouse Liver Repopulation After Cryopreservation" Hepatology, vol. 34, No. 4, pp. 824-833, 2001.
Dandri, M. et al. "Repopulation of Mouse Liver With Human Hepatocytes and In Vivo Infection With Hepatitis B Virus" Hepatology, vol. 33, No. 4, pp. 981-988, 2001.
Mercer, D. F. et al. "Hepatitis C virus replication in mice with chimeric human livers" Nature Medicine, vol. 7, No. 8, pp. 927-933, Aug. 2001.

(Continued)

*Primary Examiner* — Janice Li
(74) *Attorney, Agent, or Firm* — Oblon, McClelland, Maier & Neustadt, L.L.P.

(57) ABSTRACT

A chimeric non-human animal having an in vivo human hepatocyte population, wherein the effects of non-human animal cells on drug metabolism are suppressed or deleted is provided. A method for producing a chimeric non-human animal that lacks a drug-metabolizing system or has a suppressed drug-metabolizing system and is provided with a drug-metabolizing system driven by human hepatocytes, is provided. The method comprises transplanting human hepatocytes into a non-human animal characterized by (i) being immunodeficient, (ii) having liver damage, and (iii) lacking the functions of an endogenous Cyp3a gene.

12 Claims, 13 Drawing Sheets
(2 of 13 Drawing Sheet(s) Filed in Color)

(56) References Cited

OTHER PUBLICATIONS

Tateno, C. et al. "Near Completely Humanized Liver in Mice Shows Human-Type Metabolic Responses to Drugs" American Journal of Pathology, vol. 165, No. 3, pp. 901-912, Sep. 2004.
International Search Report Issued Dec. 4, 2012 in PCT/JP12/077019 Filed Oct. 12, 2012.
Extended European Search Report issued Jun. 1, 2015 in Patent Application No. 12840420.9.
Stephen C. Strom, et al., "Chimeric Mice with Humanized Liver: Tools for the Study of Drug Metabolism, Excretion, and Toxicity" Methods Mol Biol, vol. 640, XP002691750, 2010, 16 pages.
Philip Meuleman, et al., "Morphological and Biochemical Characterization of a Human Liver in a uPA-SCID Mouse Chimera" Hepatology, vol. 41, No. 4, 2005, pp. 847-856.
Robert A. B. van Waterschoot, et al., "Inhibition and Stimulation of Intestinal and Hepatic CYP3A Activity: Studies in Humanized CYP3A4 Transgenic Mice Using Triazolam" Drug Metabolism and Disposition, vol. 37, No. 12, XP055189423, 2009, 11 pages.
Antonius E. van Herwaarden, et al., "Knockout of cytochrome P450 3A yields new mouse models for understanding xenobiotic metabolism" Journal of Clinical Investigation, vol. 117, No. 11, XP002515970, 2007, pp. 3583-3592.
Japanese Office Action issued Aug. 25, 2015 in corresponding Japanese Patent Application No. 2011-226233, 2 pp.
Minophagen Medical Review, 2008, vol. 53, No. 1, 14 pp., "Application of Humanized Mice with Human Hepatocytes for Development of New Medicine", PhoenixBio Co., Ltd., (Includes English Language Summary).

\* cited by examiner

Fig. 1
(a)
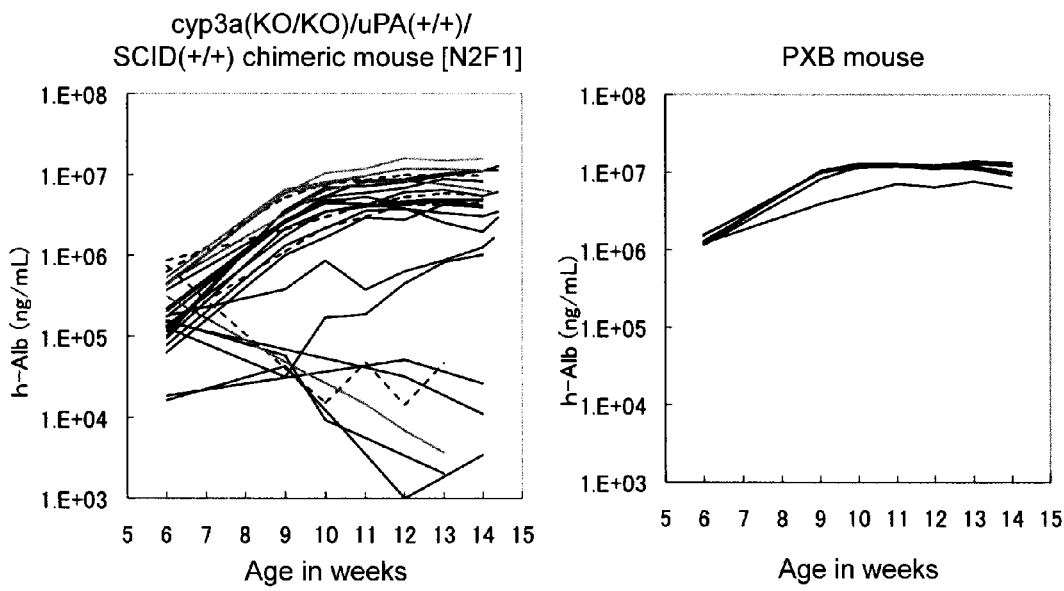
(b)
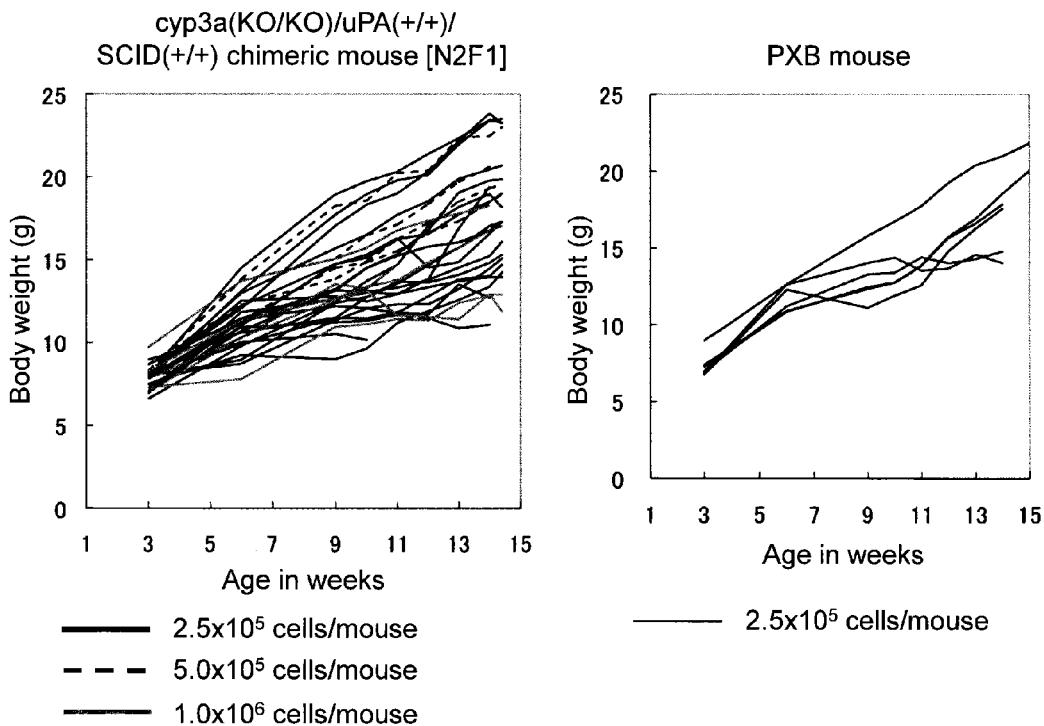
— 2.5x10⁵ cells/mouse
- - - 5.0x10⁵ cells/mouse
— 1.0x10⁶ cells/mouse
— 2.5x10⁵ cells/mouse

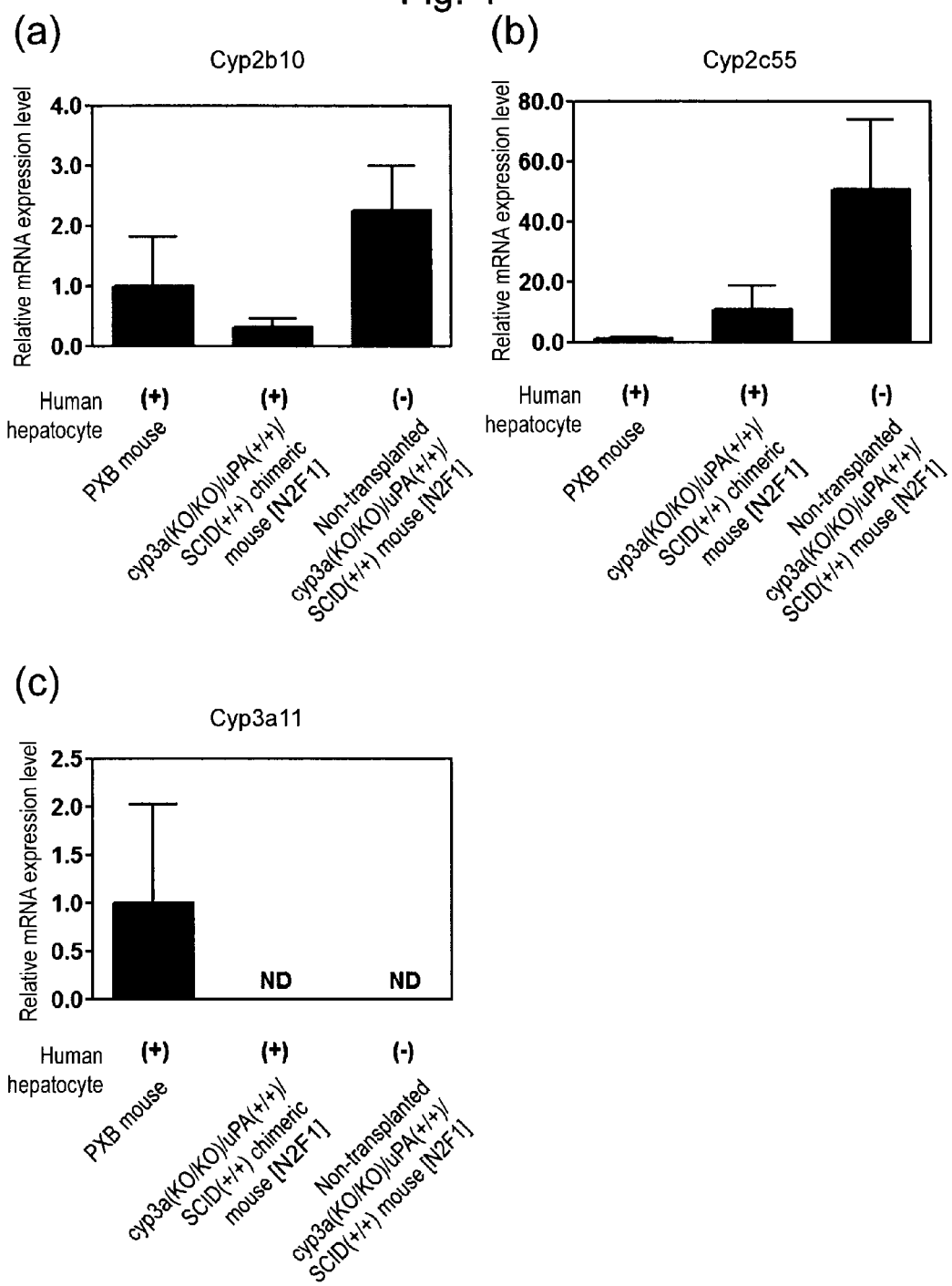

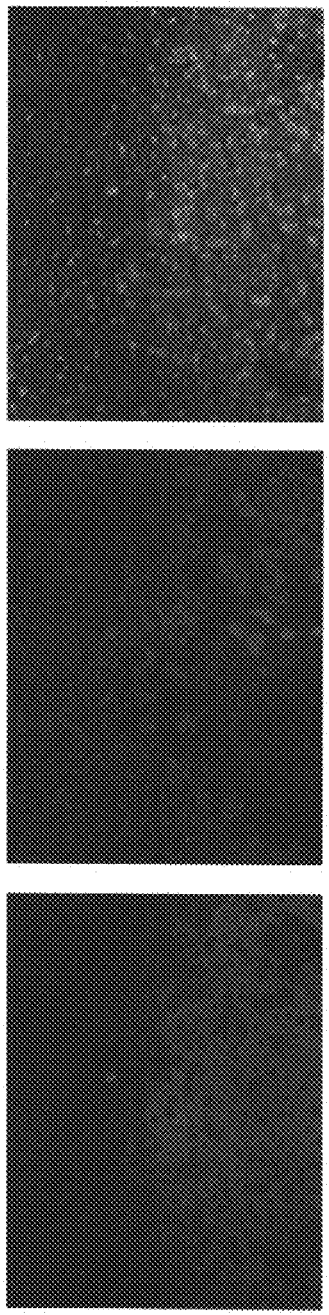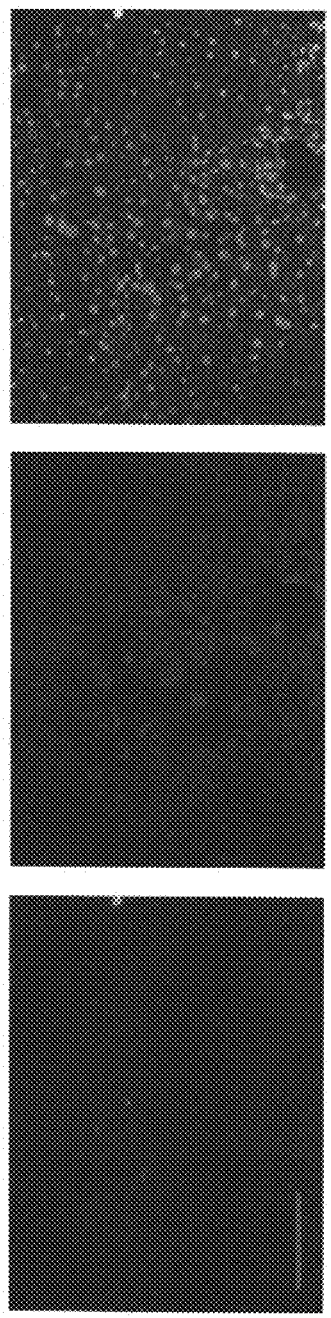

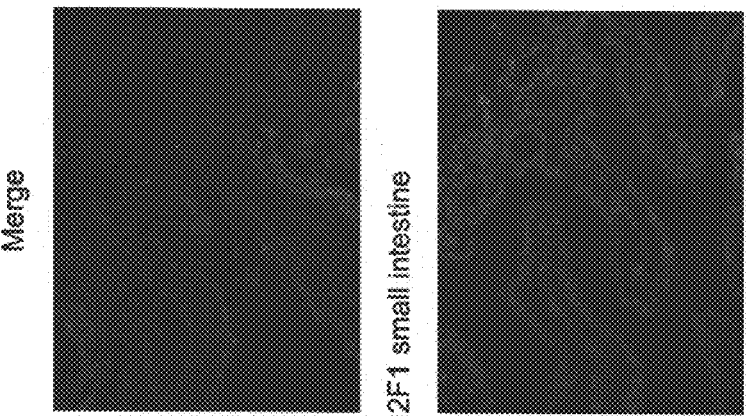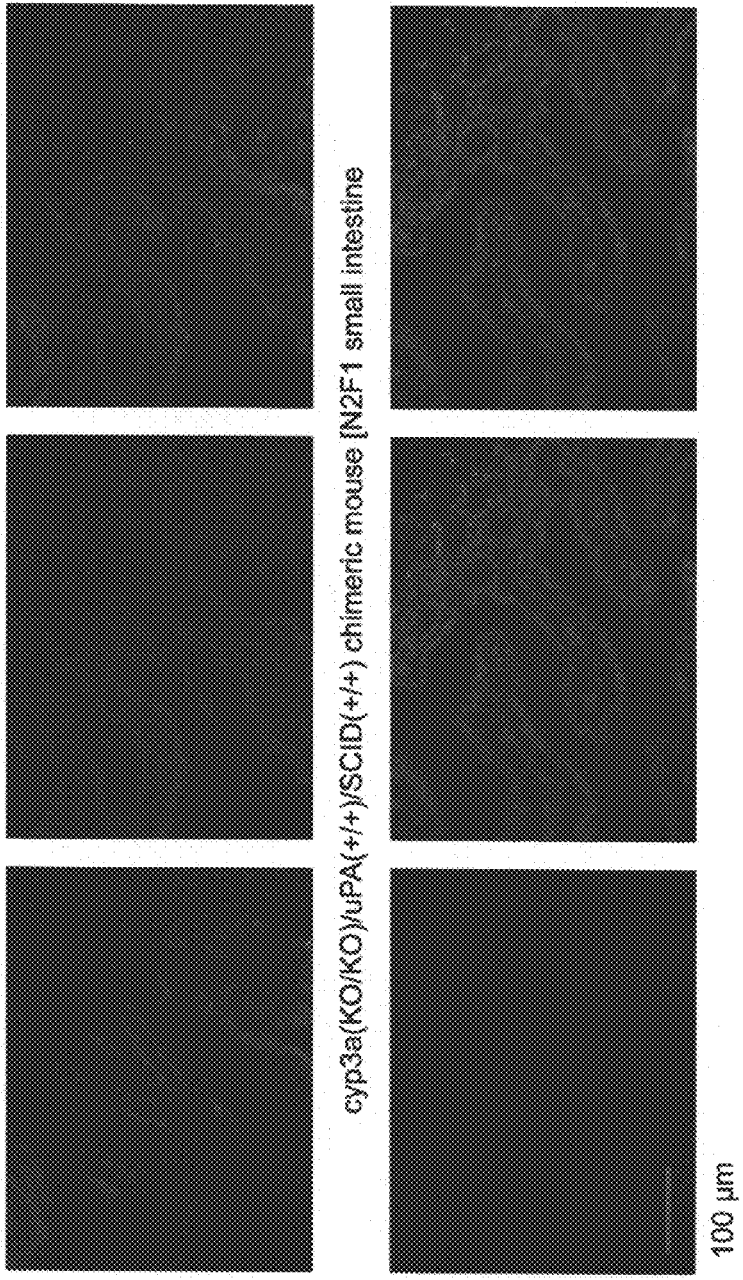

Fig. 7
(a)
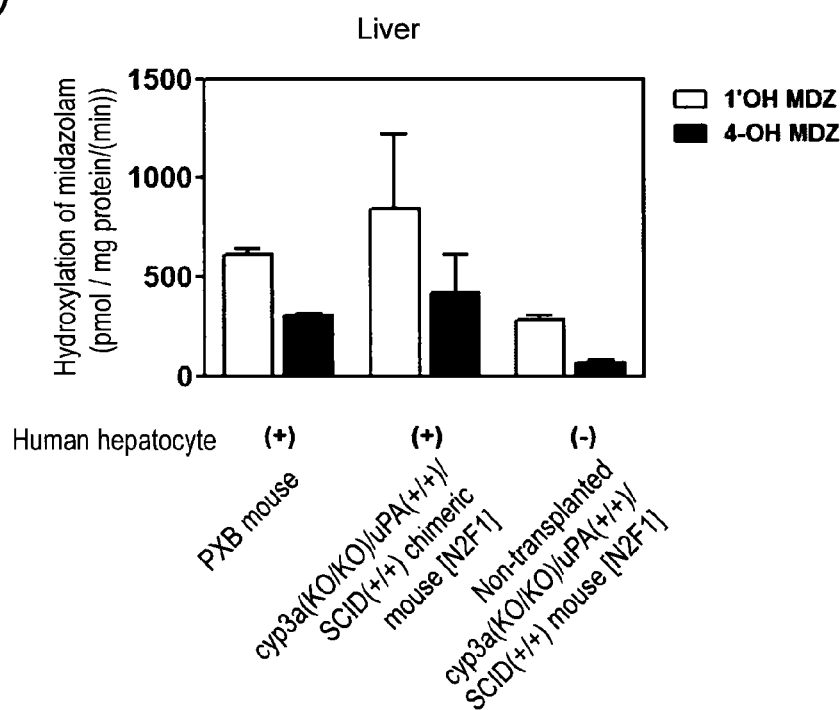
(b)
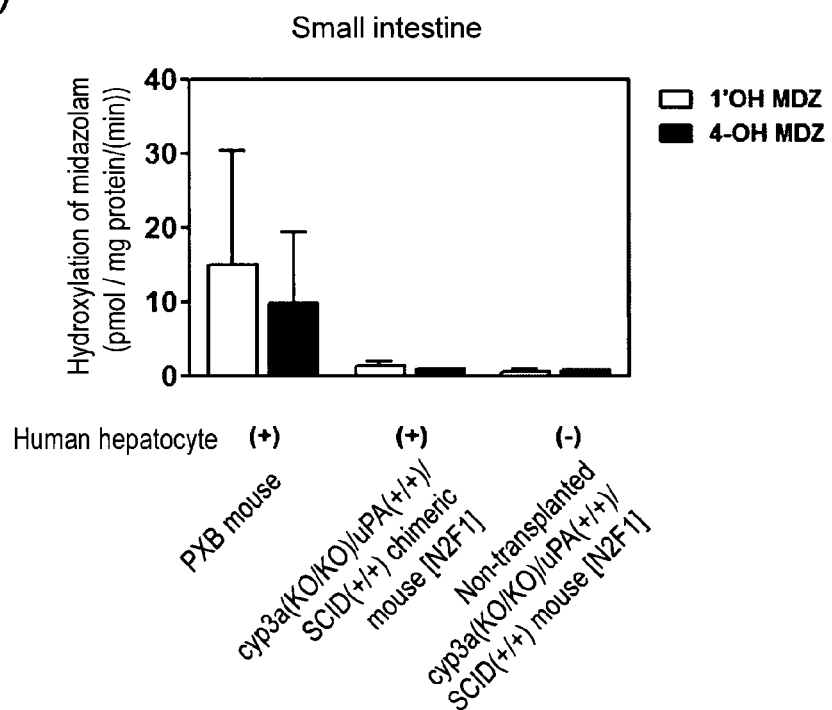

(a)

(b)

CHIMERIC NON-HUMAN ANIMAL CARRYING HUMAN HEPATOCYTE

TECHNICAL FIELD

The present invention relates to a chimeric non-human animal having an in vivo human hepatocyte population in which the effects of the non-human animal cells on drug metabolism are suppressed or deleted, and a method for producing the chimeric non-human animal.

BACKGROUND ART

In the current field of pharmaceutical development, tests to determine beneficial effects and safety studies are conducted using non-human animals such as mice, rats, dogs, or monkeys in order to select candidate drugs from many chemical substances. Clinical trials are performed for candidate drugs, the effectiveness and safety of which have been confirmed by such studies and tests using these animals. However, it is known that animals and humans differ significantly in their capacity to metabolize chemical substances and drugs. Accordingly, even in the case of a candidate drug, the effectiveness and safety of which have been confirmed by animal studies, no beneficial effect may be observed, or toxicity may occur in clinical trials. This is a major issue in the pharmaceutical development field.

Various enzymes that catalyze oxidation, reduction, or the like are involved in the in vivo metabolism of chemical substances. One of the most important enzymes is an oxidase referred to as cytochrome P450 (hereinafter, referred to as "CYP" or "Cyp"). CYP is mainly present in the liver, playing an important role in the in vivo metabolism of chemical substances and drugs in humans and animals.

Various types of CYP have been confirmed to date, and they are classified into families and then into subfamilies based on the homology of their amino acid sequences (Non-patent Literature 1).

CYPs exhibit different properties in humans and animals, even if they belong to the same subfamily. Specifically, differences have been confirmed in the substances to be used as substrates and metabolites. Therefore, it is considered that information obtained with the use of animals concerning the metabolism of a chemical substance or a drug cannot be directly applied to humans.

Because of this problem, the U.S. Food and Drug Administration recommends that in vitro tests be conducted using cultured human hepatocytes in preclinical trials. However, cultured hepatocytes do not have functions equivalent to those of the liver in vivo, and thus the precise prediction of human in vivo metabolism of chemical substances or drugs based on an in vitro test system is difficult.

Consequently, in vivo test systems prepared by transplanting human hepatocytes into animals have been developed (Patent Literature 1, Non-patent Literature 2-6). However, such in vivo test systems are problematic since the livers of host animals cannot be completely substituted with transplanted human hepatocytes. As a result, the metabolism of a given drug can still be affected by remaining host hepatocytes. Therefore, such in vivo test systems are insufficient as animal models for the precise evaluation of the capacity of human hepatocytes to metabolize chemical substances and drugs.

Hence, the development of a new test system that reflects the human metabolic system for drugs and chemical substances is still desirable in the art.

PRIOR ART LITERATURE

Patent Literature

Patent Literature 1: JP Patent Publication (Kokai) No. 2002-45087 A

Non-Patent Literature

Non-patent Literature 1: Nelson et al., Pharmacogenetics, 6: 1, 1996
Non-patent Literature 2: Rhim J A et al., Proc Natl Acad Sci U.S.A., 1995, 92: 4942-4946
Non-patent Literature 3: Dandri M et al., Hepatology, 2001, 34: 824-833
Non-patent Literature 4: Dandri M et al., Hepatology, 2001, 33: 981-988
Non-patent Literature 5: Mercer D F et al., Nat Med, 2001, 7: 927-933
Non-patent Literature 6: Tateno C et al., Am J Pathol 165: 901-912, 2004

SUMMARY OF THE INVENTION

An object of the present invention is to provide a chimeric non-human animal having a human hepatocyte population in vivo, wherein the effects of the endogenous cells of the non-human animal on drug metabolism are suppressed or deleted.

As a result of intensive studies to achieve the above object, the present inventors have discovered that a chimeric non-human animal that reflects a human drug-metabolizing system can be obtained by substituting a hepatocyte population in the liver of a non-human animal in which the functions of the endogenous Cyp genes have been deleted or suppressed, with a human hepatocyte population. Therefore, they have completed the present invention.

The present invention encompasses the following [1] to [12].

[1] A method for producing a chimeric non-human animal that lacks a drug-metabolizing system or has a suppressed drug-metabolizing system and is provided with a drug-metabolizing system driven by human hepatocytes, which comprises transplanting human hepatocytes into a non-human animal characterized by (i) being immunodeficient, (ii) having liver damage, and (iii) lacking the functions of an endogenous Cyp3a gene.

[2] The method according to [1], wherein the non-human animal is a mouse.

[3] The method according to [1] or [2], wherein the non-human animal is obtained by a production method comprising a step of performing three-way crossing of a non-human animal or offspring thereof having genetic immunodeficiency, a non-human animal or offspring thereof genetically having liver damage, and a non-human animal or offspring thereof genetically lacking the functions of the endogenous Cyp3a gene.

[4] The method according to [1] or [2], wherein the non-human animal is obtained by a production method comprising a step of crossing a non-human animal or offspring thereof having genetic immunodeficiency and genetically having liver damage and a non-human animal or offspring thereof genetically lacking the functions of the endogenous Cyp3a gene.

[5] The method according to any one of [1] to [4], wherein the non-human animal is obtained by a production method comprising steps of crossing a uPA(+/+)/SCID(+/+) mouse and a cyp3a (KO/KO) mouse, and screening for an animal that homozygously has each genetic component.

[6] The method according to any one of [1] to [5], wherein the non-human animal is a cyp3a (KO/KO)/uPA(+/+)/SCID(+/+) mouse.

[7] A chimeric non-human animal, which is obtained by the method according to any one of [1] to [6].

[8] A chimeric non-human animal, which is characterized by lacking the functions of the endogenous Cyp3a gene, and carrying in vivo human hepatocytes.

[9] The chimeric non-human animal according to [8], which lacks a drug-metabolizing system or has a suppressed drug-metabolizing system and is provided with a drug-metabolizing system driven by human hepatocytes.

[10] The chimeric non-human animal according to [8] or [9], wherein the non-human animal is a mouse.

[11] A method of conducting a toxicity study on a test substance, comprising steps of: administering a test substance to the chimeric non-human animal according to any one of [7] to [10]; and evaluating the effects of the test substance on the human hepatocytes.

[12] A method for testing the capacity of human hepatocytes to metabolize a test substance, comprising steps of:

administering a test substance to the chimeric non-human animal according to any one of [7] to [10]; and evaluating the capacity of human hepatocytes to metabolize the test substance.

According to the present invention, a chimeric non-human animal having an in vivo human hepatocyte population, wherein the effects of non-human animal cells on the drug metabolism are suppressed or deleted can be provided.

This description includes all or part of the contents as disclosed in the description and/or drawings of Japanese Patent Application No. 2011-226233, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necesssry fee.

FIG. 2-1 shows the expression levels (mean±SD (n=3)) of mRNA encoding human CYP1A2, 2B6, 2C8, 2C9, 2C19, 2D6 and 3A4 in the liver of PXB mice, cyp3a (KO/KO)/uPA(+/+)/SCID(+/+) chimeric mice [N2F1] and non-transplanted cyp3a (KO/KO)/uPA(+/+)/SCID(+/+) mice [N2F1]. Each expression level is relative to the level in the PXB mice, designated as "1". No detection is denoted as ND (not detected).

FIG. 2-2 is a continuation of FIG. 2-1.

FIG. 3-1 shows the expression levels (mean±SD (n=3)) of mRNA encoding mouse Cyp1a2, 2b10, 2c29, 2c37, 2c55 and 3a11 in the liver of PXB mice, cyp3a (KO/KO)/uPA(+/+)/SCID(+/+) chimeric mice [N2F1], and non-transplanted cyp3a (KO/KO)/uPA(+/+)/SCID(+/+) mice [N2F1]. Each expression level is relative to the level in the PXB mice, designated as "1". No detection is denoted as ND (not detected).

FIG. 3-2 is a continuation of FIG. 3-1.

FIG. 4 shows the expression levels (mean±SD (n=3)) of mRNA encoding mouse Cyp2b10, 2c55 and 3a11 in the small intestine of PXB mice, cyp3a (KO/KO)/uPA(+/+)/SCID(+/+) chimeric mice [N2F1] and non-transplanted cyp3a (KO/KO)/uPA(+/+)/SCID(+/+) mice [N2F1]. Each expression level is relative to the level in the PXB mice, designated as "1". No detection is denoted as ND (not detected).

FIG. 5 shows the results of immunostaining of the liver of PXB mice (FIGS. 5A-5C) and cyp3a (KO/KO)/uPA(+/+)/SCID(+/+) chimeric mice [N2F1] (FIGS. 5D-5F) using a human specific cytokeratin 8/18 (hCK8/18) antibody and a mouse Cyp3a antibody.

FIG. 6 shows the results of immunostaining of the small intestine of PXB mice (FIGS. 6A-6C) and cyp3a (KO/KO)/uPA(+/+)/SCID(+/+) chimeric mice [N2F1] (FIGS. 6A-6C) using a mouse Cyp3a antibody and Hoechst (nuclear staining).

FIG. 7 shows the results of measuring midazolam (MDZ) metabolic activity (mean±SD (n=3)) using microsomes from the liver (a) and the small intestine (b) of PXB mice, cyp3a (KO/KO)/uPA(+/+)/SCID(+/+) chimeric mice [N2F1] and non-transplanted cyp3a (KO/KO)/uPA(+/+)/SCID(+/+) mice [N2F1].

FIG. 8-1 shows the blood human albumin (h-Alb) concentrations (FIG. 8-1($a$)), body weights (FIG. 8-1($b$)), and a graph (FIG. 8-2($c$)) of the correlation between h-Alb and the rate [RI(%)] of replacement of the liver with human hepatocytes in the case of cyp3a (KO/KO)/uPA(+/+)/SCID(+/+) mice [N4F1] into which human hepatocytes have been transplanted.

FIG. 8-2 is a continuation of FIG. 8-1.

FIG. 9-1 shows the metabolite profiles of nefazodone in blood plasma (FIG. 9-1($a$)) and urine (FIG. 9-1($b$)) of cyp3a (KO/KO)/uPA(+/+)/SCID(+/+) mice [N4F1] into which human hepatocytes have been transplanted, PXB mice and SCID(+/+) mice. Metabolites characteristic of humans are denoted as "human metabolites."

FIG. 9-2 is a continuation of FIG. 9-1.

MODES FOR CARRYING OUT THE INVENTION

Figures 1, 2:
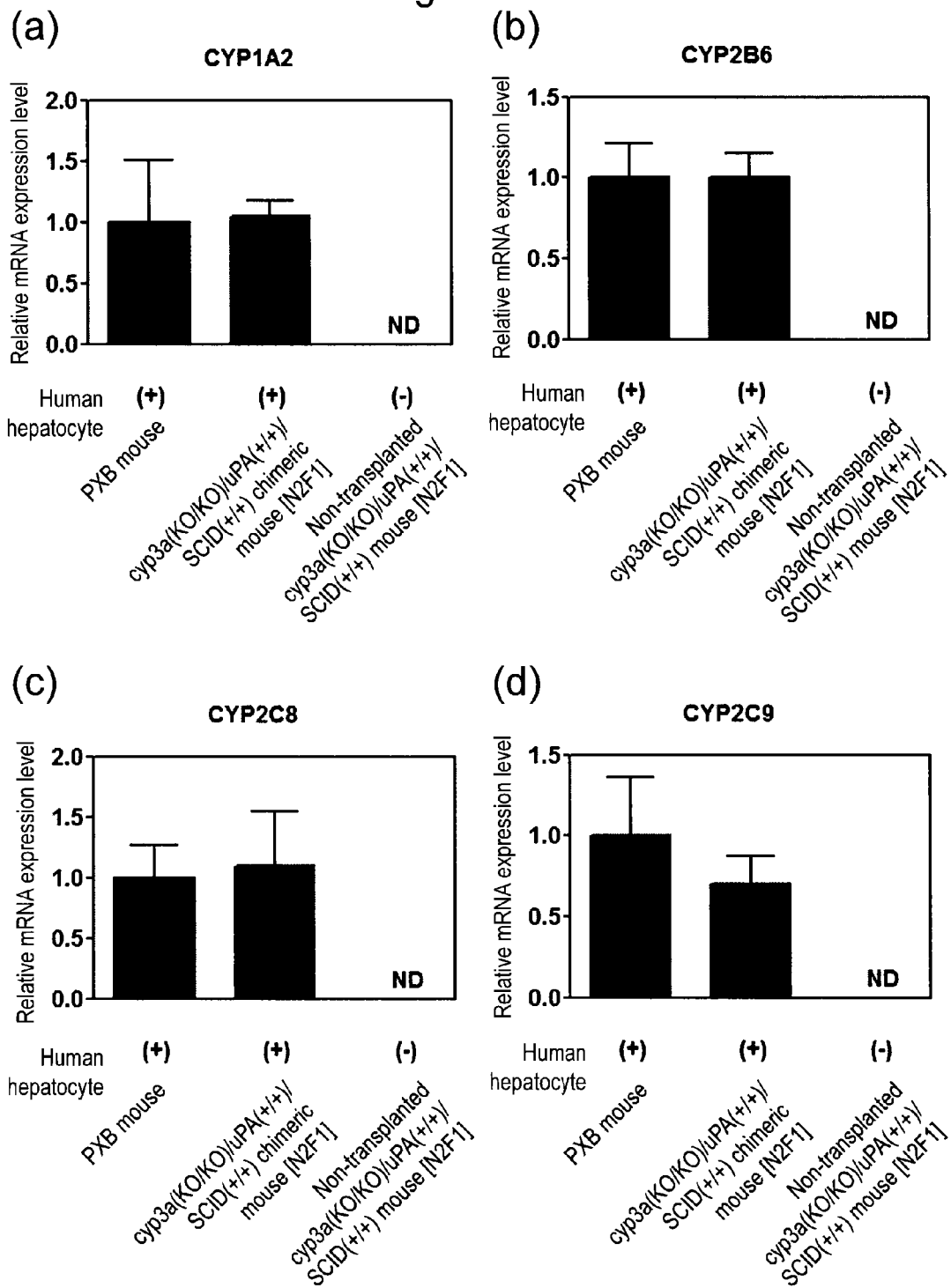
Figure 2:
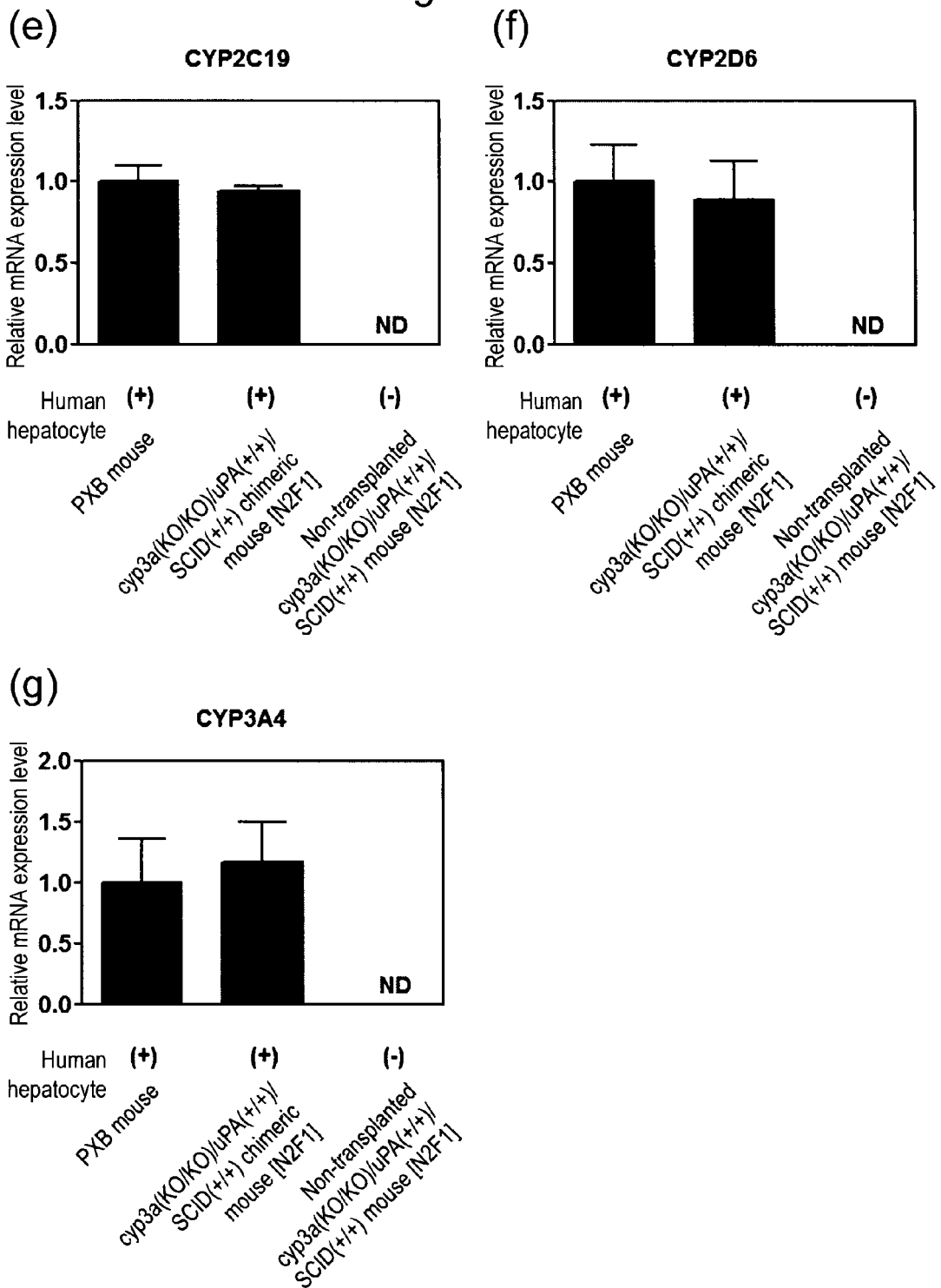

A chimeric non-human animal in the present invention can be prepared by transplanting human hepatocytes into a non-human animal characterized by (i) being immunodeficient, (ii) having liver damage, and (iii) lacking the functions of one or a plurality of endogenous Cyp genes.

Here, an example of "non-human animal" include mammals excluding humans and are preferably mammals classified as rodents. Examples of mammals classified as rodents include, but are not limited to, mice and rats. Preferably, the term "a non-human animal(s)" in the present invention refers to "a mouse (mice)."

The term "immunodeficient or immunodeficiency" as used herein means that no rejection is exhibited against cells (particularly, hepatocytes) from a heterologous animal. Immunodeficiency may be acquired after birth by subjecting the non-human animal to treatment to cause immunodeficiency, such as administration of an immunosuppressive agent or thymectomy. Preferably, the non-human animal is congenitally immunodeficient. Specifically, the non-human animal is preferably an animal with genetic immunodeficiency or offspring thereof. Examples of "animal with genetic immunodeficiency" include, but are not limited to, animals with severe combined immunodeficiency (SCID) exhibiting T-cell deficiency and B-cell deficiency, animals that have lost T cell functions due to genetic athymia, and animals produced by knocking out the RAG2 gene by a known gene targeting method (Science, 244: 1288-1292, 1989). Examples thereof include SCID mice, NUDE mice, and RAG2 knockout mice and are preferably SCID mice.

The term "having liver damage" as used herein means that at least 60%, at least 70%, at least 80%, at least 90%, and at least 95% or more of the original liver cells (particularly, hepatocytes) of a non-human animal are affected, exhibit suppressed growth, and/or give rise to necrosis. When a non-human animal is affected by liver damage, transplanted human hepatocytes can efficiently engraft and/or grow. Liver damage may be acquired by subjecting a non-human animal to treatment for inducing liver damage, such as administration of a liver damage inducer (e.g., carbon tetrachloride, yellow phosphorus, D-galactosamine, 2-acetyl aminofluorene, and pyrrolizidine alkaloid) and surgical treatment (e.g., partial hepatectomy). The non-human animal is preferably an animal congenitally having liver damage. Specifically, the non-human animal is preferably an animal genetically having liver damage or offspring thereof. Examples of such an "animal genetically having liver damage" include, but are not limited to, transgenic animals expressing a liver damage-inducing protein under the control of an enhancer and/or a promoter of a protein that is expressed in a hepatocyte-specific manner and animals in which genes responsible for liver functions have been knocked out. Examples thereof include transgenic mice expressing a urokinase plasminogen activator (uPA), a tissue plasminogen activator (tPA), a thymidine kinase (tk), and the like in a liver-specific manner, and fumarylacetoacetate hydrolase (Fah) gene-knockout mice. A drug for inducing liver damage may be administered to an animal genetically having liver damage, if necessary (for example, ganciclovir (GCV) can be administered to a transgenic mouse expressing thymidine kinase (tk) in a liver-specific manner).

The expression "lacking the functions of one or a plurality of endogenous Cyp genes" as used herein means the lack of the normal expression and/or the functions of functional proteins encoded by the Cyp gene(s) due to a mutation such as substitution, deletion, addition or insertion of nucleotides in one or a plurality of endogenous Cyp genes in the non-human animal. Specifically, the non-human animal is an animal genetically lacking the functions of one or a plurality of endogenous Cyp genes, or offspring thereof.

CYPs form a super family that is broadly classified into 4 groups. Specifically, CYPs are each classified into a family and then to a subfamily based on the amino acid sequence. In the present invention, the term "Cyp gene(s)" can be selected from the super family, families or subfamilies. In the present invention, the term "Cyp gene" refers to a Cyp gene(s) that contributes to the metabolism of pharmaceutical products or chemical substances, such as a Cyp1 gene, a Cyp2 gene, a Cyp3 gene, and a Cyp4 gene. Preferable examples thereof include a Cyp1a gene, a Cyp1b gene, a Cyp1e gene, a Cyp2a gene, a Cyp2c gene, a Cyp2d gene, a Cyp3a gene, and a Cyp4a gene. A more preferable example thereof is the Cyp3a gene. CYP3A is known as a representative drug-metabolizing enzyme that contributes to the metabolism of many pharmaceutical products and chemical substances, for example.

In general, Cyp genes have the structure of a gene cluster encoding a plurality of molecular species. The number of molecular species to be encoded by Cyp genes may vary depending on the non-human animal to be used, or the super family or the family. In the present invention, the expression and/or the functions of all molecular species to be encoded by selected Cyp genes may be deleted, or the expression and/or the functions of molecular species to be encoded may be partially deleted. For example, when the non-human animal is a mouse, the Cyp3a gene encodes molecular species including Cyp3a11, Cyp3a13, Cyp3a16, Cyp3a25, Cyp3a41, Cyp3a44, Cyp3a57, Cyp3a59, and the like, and the expression and/or the functions of 1, 2, 3, 4, 5, 6, 7, 8 or more molecular species thereof can be deleted. For example, the expression and/or the functions of at least Cyp3a11, Cyp3a13, Cyp3a25, and Cyp3a44 are deleted. Preferably, the expression and/or the functions of all the molecular species encoded by the Cyp3a gene are deleted.

The functions of Cyp genes can be deleted by a gene targeting method that is generally employed in the art, for example. Deletion of the gene functions can be confirmed by general techniques known by persons skilled in the art. For example, such deletion of the functions can be confirmed by performing Southern analysis, PCR, or the like with the use of genomic DNA extracted from the obtained non-human animal to confirm a mutation such as substitution, deletion, addition or insertion of nucleotides in endogenous Cyp gene(s). Furthermore, such deletion of the functions can also be confirmed by confirming the deletion of the expression of target Cyp genes using an RT-PCR method.

A non-human animal with the above characteristics (i) to (iii) can be obtained by crossing an animal or offspring thereof with the above genetic immunodeficiency, an animal or offspring thereof genetically having liver damage, and an animal or offspring thereof genetically lacking the functions of endogenous Cyp gene(s), all of which are of the same species; that is, performing three-way crossing of these animals. The characteristics of these animals are each passed to the next generation in the form of genetic component according to Mendel's laws. Animals to be used for crossing may be a homozygote or a heterozygote in terms of the genetic component relating to each characteristic. Combinations for crossing include various patterns, for example, a non-human animal with the above characteristics (i) to (iii) can be obtained by the following method (however, the examples thereof are not limited to this one).

Specifically, offspring are obtained by crossing an animal or offspring thereof having genetic immunodeficiency and an animal or offspring thereof genetically having liver damage, one or a plurality of self-crossing and back-crossing are performed according to a conventional method, and thus animals homozygously or heterozygously having a genetic component relating to each characteristic are obtained. Subsequently, offspring are obtained by crossing the thus obtained animals and an animal or offspring thereof genetically lacking the functions of endogenous Cyp gene(s). If necessary, one or a plurality of self-crossing and back-crossing are performed according to a conventional method, and then animals that are homozygotes in terms of various characteristics are finally selected. The present inventors have already reported the preparation of immunodeficient uPA(+/+)/SCID(+/+) mice with liver damage (WO2008/001614). The present inventors have also already reported the preparation of cyp3a (KO/KO) mice genetically lacking the functions of the endogenous Cyp3a gene (WO2009/063722). In the above crossing, these mice can be preferably used.

Human hepatocytes to be used for transplantation into a non-human animal with the above characteristics (i) to (iii) can be prepared based on conventionally known techniques. Specifically, human hepatocytes can be isolated from normal human liver tissue using a collagenase perfusion method. Human hepatocytes isolated from humans at various ages can be used, however it is preferable to use hepatocytes from human infants under the age of 14, as these can grow well in the liver tissue of a chimeric non-human animal after transplantation and can increase the fraction of human hepatocytes.

As human hepatocytes, proliferating human hepatocytes that exhibit high proliferative capacity in vivo can also be used herein. The term "proliferating human hepatocytes" refers to human hepatocytes that grow (clonal proliferation) while forming colonies consisting of populations of single cell species under culture conditions (in vitro). The number of proliferating human hepatocytes can be increased by subculture. Proliferating human hepatocytes can be used for transplantation after the number thereof is sufficiently increased by subculture.

Examples of proliferating human hepatocytes include, but are not limited to, human small hepatocytes (JP Patent Publication (Kokai) No. H10-179148 A (1998)). Human small hepatocytes possess high proliferative capacity, as well as capacity to differentiate into hepatocytes having various liver functions since they are relatively undifferentiated cells. Human small hepatocytes rapidly grow in vivo in a non-human animal into which these hepatocytes have been transplanted, and thus are capable of forming within a short time a human hepatocyte population that can exhibit normal liver functions.

Human small hepatocytes can be prepared based on conventionally known techniques. Specifically, a method using centrifugation, a method using a cell fractionation device such as an elutriator or FACS, an immunological technique using a monoclonal antibody that specifically recognizes human small hepatocytes, and the like can be used (JP Patent Publication (Kokai) No. H10-179148 A (1998), and JP Patent Publication (Kokai) No. H08-112092 A (1996)).

Moreover, as human hepatocytes to be used for transplantation, hepatitis virus-infected cells or hepatocytes from a patient having genetic disorder can be used. A chimeric non-human animal obtained by transplantation of such hepatocytes presents with symptoms similar to those of the patient, so that it can be used as a "pathological model animal" for hepatitis or other diseases, and is useful in tests for development of antiviral agents or drugs against diseases.

Furthermore, as other human hepatocytes to be used for transplantation, human hepatocytes proliferated in vitro, cryopreserved hepatocytes, hepatocytes immortalized by introduction of a telomerase gene or the like, and a mixture of such hepatocytes with non-parenchymal cells can also be used herein.

The thus prepared human hepatocytes can also be transplanted into the above non-human animal by the following techniques.

Human hepatocytes are injected into the spleen or a portal vein of the above non-human animal to allow the cells to be transplanted into the liver of the non-human animal via the spleen or a portal vein. The number of human hepatocytes to be used for transplantation can range from about 1 to 2,000,000, and preferably about 100,000 to 1,000,000. About 5% to 15% and preferably about 10% of transplanted human hepatocytes enter the hepatic cell cord from the sinusoid of the non-human animal, engraft, and grow.

The age in days of a non-human animal to which the above human hepatocytes are transplanted is not particularly limited, and preferably a non-human animal at lower age in days or weeks is used. Through transplantation of human hepatocytes into a non-human animal at lower age in days or in weeks, the thus transplanted human hepatocytes can engraft and grow successfully. When a mouse is used as a non-human animal, it should be within about 0 to 48 days of life; and preferably within about 8 to 28 days of life.

A chimeric non-human animal to which human hepatocytes have been transplanted can be kept by a conventional method. After transplantation, such a chimeric non-human animal is kept for about 40 to 200 days, and thus 50%, 60%, 70%, 75%, 80%, 85%, 90%, 95%, 99% or more of hepatocytes in the liver will be substituted with human hepatocytes. Human hepatocytes can be detected by techniques known in the art, such as an immunological technique using an antibody specific to human hepatocytes.

The liver in the chimeric non-human animal of the present invention comprises human hepatocytes accounting for 50%, 60%, 70%, 75%, 80%, 85%, 90%, 95%, 99% or more of all hepatocytes in the liver and also contains non-parenchymal cells of the non-human animal (e.g., sinusoidal endothelial cells, stellate cells, and Kupffer cells) as portions.

The liver in the chimeric non-human animal of the present invention expresses human drug-metabolizing enzymes. Examples of such a "human drug-metabolizing enzyme" include CYPs and the like. For example, molecular species such as at least CYP1A2, CYP2B6, CYP2C8, CYP2C9, CYP2C19, CYP2D6, and CYP3A4 can be detected (examples thereof are not limited to them). Such molecular species can be detected by methods that are generally employed for nucleic acid analysis, such as RT-PCR and Northern blotting.

Furthermore, the liver in the chimeric non-human animal of the present invention is deficient in the functions of one or a plurality of endogenous Cyp genes of the non-human animal. Moreover, in the liver of the chimeric non-human animal of the present invention, increases in compensatory expression of other Cyp genes resulting from the lack of the functions of some Cyp genes are significantly suppressed. In general, it is known that in Cyp3a knockout mice, the expression levels of various endogenous Cyp genes, including the Cyp2 gene are increased (van Waterschoot R A et al., Mol Pharmacol, 2008, 73: 1029-1036). Meanwhile, as described in detail in the following Examples, the liver of a chimeric non-human animal obtained using a Cyp3a gene-deficient non-human animal (mouse) lacked the expression of a plurality of molecular species encoded by the endogenous Cyp3a gene of the non-human animal, and exhibited significantly lower expression levels of other endogenous Cyp genes than those of Cyp3a knockout mice.

As described above, the liver in the chimeric non-human animal of the present invention is capable of reducing or eliminating the interference of endogenous Cyp molecular species of the non-human animal while expressing a human drug-metabolizing enzyme. Hence, the liver is provided with physiological characteristics, in particular the drug metabolism profiles, similar or identical to those of human liver.

The fact that the liver of the chimeric non-human animal of the present invention has the human liver-type drug metabolism profiles can be confirmed by the following techniques. Specifically, a specific compound is administered to the above chimeric non-human animal and a human and/or non-human animal, a metabolite of the compound in a sample from each of the animals and humans is detected and identified, and then a metabolite detected and identified in the sample from the chimeric non-human animal is compared with a metabolite detected and identified in the sample from the human and/or non-human animal, so as to determine if the metabolic profiles of the chimeric non-human animal are of human type or non-human animal type.

An example of a compound to be used for the above method is, but is not limited to, nefazodone (Mayol R F et al, Drug Metab Dispos 22(2): 304-11, 1994). Compounds, the metabolic profiles of which in a human or a non-human animal are known, can also be used herein. As samples, body fluids such as blood (plasma, serum), urine, lymph, and bile, liver, other organs, and feces can be used herein. Various types of chromatography and mass spectroscopy methods known in the art can be adequately used in combination for detection and identification of a metabolite in such a sample. For example, as described in detail in the following Examples, when nefazodone is administered to the chimeric non-human animal of the present invention, metabolic profiles exhibited herein are more similar to those of human type than to those of a non-human animal (mouse). Therefore, whether the resulting metabolic profiles are of human type or non-human animal type can be easily determined.

As in the liver, CYP is also present in the small intestine and involved in drug metabolism. The small intestine of the chimeric non-human animal of the present invention is deficient in the functions of one or a plurality of endogenous Cyp genes of the non-human animal. Furthermore, in the small intestine of the chimeric non-human animal of the present invention, increases in compensatory expression of other Cyp genes resulting from the lack of the functions of some Cyp genes are significantly suppressed. In general, it is known that in Cyp3a knockout mice, the expression levels of various endogenous Cyp genes, including the Cyp2 gene are increased (as mentioned above). Meanwhile, as described in detail in the following Examples, the small intestine of a chimeric animal obtained using a Cyp3a gene-deficient non-human animal (mouse), the expression of a plurality of molecular species encoded by the endogenous Cyp3a gene of the non-human animal has been deleted, and the expression levels of other endogenous Cyp genes are significantly lower than those of Cyp3a knockout mice.

As described above, the chimeric non-human animal of the present invention carries in vivo human hepatocytes, and lacks an endogenous drug-metabolizing system or has a suppressed endogenous drug-metabolizing system because of the deletion of the functions of one or a plurality of endogenous Cyp genes of the non-human animal. Therefore, the chimeric non-human animal of the present invention is provided with a drug-metabolizing system driven by human hepatocytes, and thus can be preferably used as an experimental model for drug metabolism studies and toxicity studies, for example.

Drug metabolism studies and toxicity studies can be conducted by general techniques. Specifically, these studies are conducted by administering a test substance (e.g., a pharmaceutical product and a chemical substance) to the chimeric non-human animal of the present invention, and then evaluating the capacity of human hepatocytes to metabolize the administered substance and the toxicity of the administered substance against human hepatocytes. A test substance can be administered to a chimeric non-human animal via peroral administration or parenteral administration (e.g., intravenous administration, intramuscular administration, subcutaneous administration, transdermal administration, transnasal administration, and transpulmonary administration).

The capacity of human hepatocytes in a chimeric non-human animal to metabolize a test substance can be evaluated and determined by general techniques in the art. Specifically, samples (e.g., body fluids such as blood (plasma, serum), urine, lymph, and bile, liver, other organs, and feces) are collected from a chimeric animal after administration of a test substance, and then metabolites are detected, identified and/or measured. Various types of chromatography and mass spectroscopy methods can be employed for metabolite detection, identification, and measurement.

The toxicity of a test substance against human hepatocytes can be evaluated by general techniques in the art. Specifically, a portion (hepatocyte population) of the liver of a chimeric non-human animal is collected after administration of a test substance, and then observed under a microscope, so as to evaluate the condition of the liver. Alternatively, a blood (whole blood, plasma, serum) sample is collected from a chimeric animal after administration of a test substance, and then the condition of the liver can be evaluated using increases or decreases in the levels of proteins or compounds as indices for hepatocyte functions contained in blood. Examples of such "proteins or compounds that can be indices for hepatocyte functions" include, but are not limited to, albumin, choline esterase, cholesterol, γ-globulin, type-IV collagen, hyaluronic acid, and platelet.

The present invention will be further described in detail by examples as follows, but the technical scope of the present invention is not limited by these examples.

Example 1

Preparation of Cyp3a-Gene-Knockout Immunodeficient Mouse with Liver Damage

The frozen sperm of the cyp3a (KO/KO) mice (WO2009/063722) (prepared by the present inventors) was thawed. After artificial insemination of the unfertilized eggs of the uPA(+/+)/SCID(+/+) mice (WO2008/001614) (prepared by the present inventors) with the sperm, the fertilized eggs were inserted to surrogate mice. Mice with the genotype of cyp3a (KO/wt)/uPA(+/wt)/SCID(+/wt) [F1] were selected from the offspring, and then subjected to second back-crossing with uPA(+/+)/SCID(+/+) mice by natural crossing, thereby obtaining cyp3a (KO/wt)/uPA(+/+)/SCID(+/+) mice [N2].

The uPA genotype and the SCID genotype were identified according to conventionally known techniques (WO 2008/001614). Specifically, the uPA genotype was identified by a genomic PCR method using primers containing sequences specific to the uPA gene, and the SCID genotype was identified by a PCR-RFLP method. The Cyp3a genotype was identified by extracting genomic DNA from the tail of the mouse offspring, and then performing a genomic PCR method (transferred to Chromocenter, Inc). On the basis of the results of the genomic PCR method, cyp3a (KO/wt)/uPA(+/+)/SCID (+/+) mice and/or cyp3a (KO/KO)/uPA(+/+)/SCID(+/+) mice having experienced no homologous chromosome crossing-over were selected. In addition, the recombination rate due to homologous chromosome crossing-over in mice (N2) was 12%.

Next, the thus obtained cyp3a (KO/wt)/uPA(+/+)/SCID (+/+) mice [N2] were crossed with each other to obtain cyp3a (KO/KO)/uPA(+/+)/SCID(+/+) mice [N2F1]. The thus obtained mice [N2F1] were used for the following human hepatocyte transplantation experiments.

Moreover, because of low engraftment and replacement rates of human hepatocytes to the cyp3a (KO/KO)/uPA(+/+)/SCID(+/+) mice [N2F1], the cyp3a (KO/wt)/uPA(+/+)/SCID (+/+)[N2] mice were further back-crossed twice to uPA(+/+)/SCID(+/+) mice by natural crossing, thereby obtaining cyp3a (KO/wt)/uPA(+/+)/SCID(+/+) mice [N3,N4]. Furthermore, the cyp3a (KO/wt)/uPA(+/+)/SCID(+/+) mice [N4] were crossed with each other, thereby obtaining cyp3a (KO/KO)/uPA(+/+)/SCID(+/+) mice [N4F1]. The thus obtained cyp3a (KO/KO)/uPA(+/+)/SCID(+/+) mice [N4F1] were also used for the following human hepatocyte transplantation experiments. In addition, the recombination rate resulting from homologous chromosome crossing-over was 12% in the case of N2F1, 0% in the case of N3, 36% in the case of N4, and ranged from 24% to 29% in the case of N4F1.

Example 2

Human Hepatocyte Transplantation 1

As human hepatocytes, hepatocytes (Lot No. BD85, boy, 2 years old) purchased from BD Gentest were used. The frozen hepatocytes were thawed by a conventionally known technique (Chise Tateno et al., Am J Pathol 165: 901-912, 2004) and then used.

Twenty nine cyp3a (KO/KO)/uPA(+/+)/SCID(+/+) mice [N2F1] (2- to 4-week-old) obtained in Example 1 were anaesthetized with ether, and then each left abdomen was incised about 5 mm. After injection of 2.5 to $10.0 \times 10^5$ human hepatocytes into the inferior splenic pole, the spleen was returned to the peritoneal cavity, and then the incision was sutured. Human hepatocytes were similarly transplanted into uPA (+/+)/SCID(+/+) mice as control mice.

Blood (2 uL each) was collected from the mouse tail vein on weeks 3 and 6 and every week after transplantation and then added to 200 uL of LX-Buffer (Eiken Chemical Co., Ltd.). The human albumin concentration in mouse blood was measured by immunonephelometry using an autoanalyzer JEOL BM6050 (JEOL Ltd.). As a result, in the cyp3a (KO/KO)/uPA(+/+)/SCID(+/+) mice into which human hepatocytes had been transplanted (hereinafter, referred to as "cyp3a (KO/KO)/uPA(+/+)/SCID(+/+) chimeric mice"), increases in human albumin concentration were observed and six mice thereof were confirmed to have a human albumin concentration of >7 mg/ml (21%, FIG. 1 (a)). In the uPA(+/+)/SCID (+/+) mice into which human hepatocytes had been transplanted (hereinafter, referred to as "PXB mice"), about 80% of the mice exhibited a human albumin concentration of >7 mg/ml, suggesting that the engraftment and replacement rates of human hepatocytes in the cyp3a (KO/KO)/uPA(+/+)/SCID (+/+) chimeric mice were lower than those of the PXB mice. Furthermore, smooth body weight gain was observed for all mice (FIG. 1 (b)).

On weeks 10 to 11 after transplantation (14-week-old), each of chimeric mice and non-transplanted cyp3a (KO/KO)/uPA(+/+)/SCID(+/+) mice [N2F1] was dissected and thus the liver, the small intestine, and blood were collected. The collected liver and small intestine were cut into appropriate sizes. The resulting pieces were immersed in 1 mL of RNA Later (Life Technologies Corporation, Cat No. AM7020), stored at 4° C. overnight, and then stored at −80° C. In addition, portions of the liver and the small intestine were embedded in an OCT compound (Tissue-Tek) for the preparation of frozen sections, and then cryopreserved with liquid nitrogen. Microsomes were prepared from the remaining small intestine and liver portions by procedures such as centrifugation. The thus prepared microsomes were stored at −80° C.

Example 3

RT-PCR Analysis of Human and Mouse Cyp mRNA Expression in the Liver

The expression levels of mRNA encoding various human or mouse CYPs and β-actin (gene for adjustment) in the liver of the cyp3a (KO/KO)/uPA(+/+)/SCID(+/+) chimeric mice [N2F1], the PXB mice, and the non-transplanted cyp3a (KO/KO)/uPA(+/+)/SCID(+/+) mice [N2F1] prepared in Example 2 above were measured using an RT-PCR method.

The results of analyzing the expression levels of mRNA encoding human CYP1A2, 2B6, 2C8, 2C9, 2C19, 2D6, and 3A4 in the liver are shown in FIG. 2-1 and FIG. 2-2.

When the cyp3a (KO/KO)/uPA(+/+)/SCID(+/+) chimeric mice [N2F1] were compared with the PXB mice for the expression levels of mRNA encoding these CYPs in the liver, the expression level in the cyp3a (KO/KO)/uPA(+/+)/SCID (+/+) chimeric mice [N2F1] accounted for about 70% to 117% of the expression level in the PXB mice, confirming that the gene expression levels were almost the same.

Figures 1, 3:
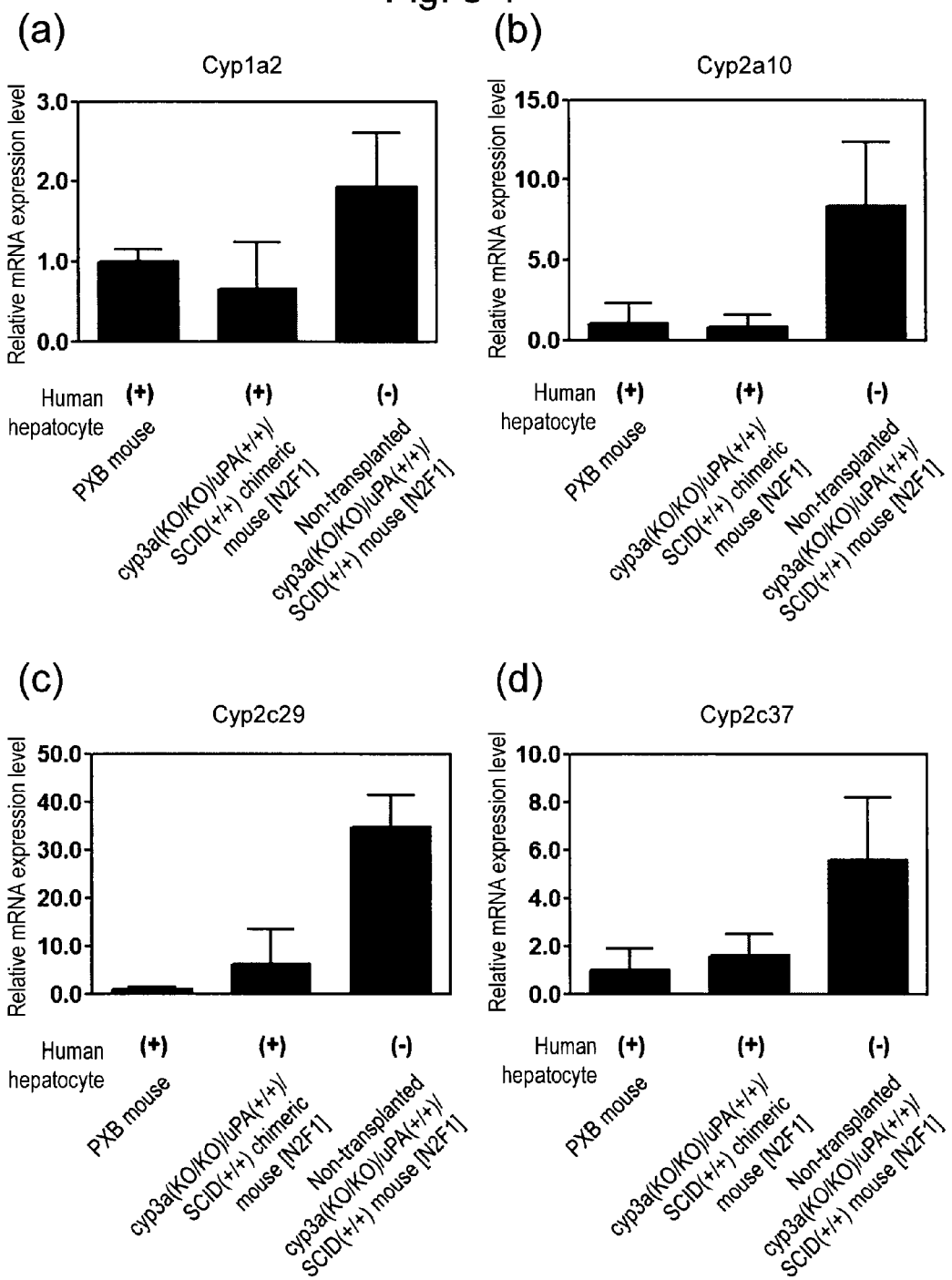
Figures 2, 3:
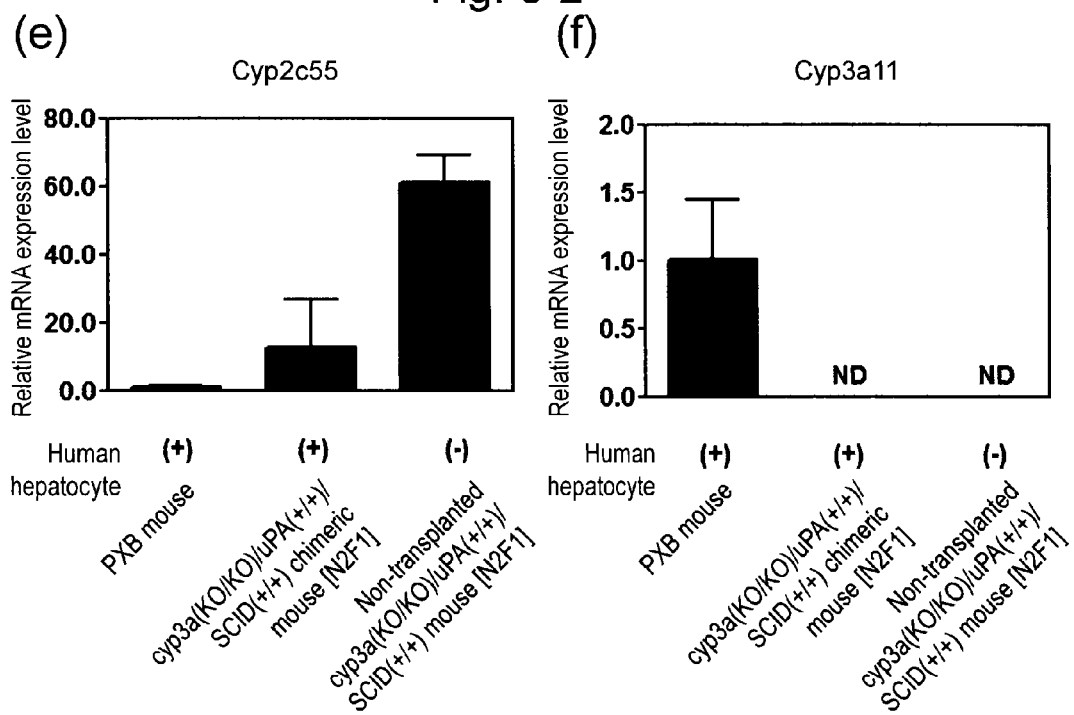

Next, the results of analyzing the expression levels of mRNA encoding mouse Cyp1a2, 2b10, 2c29, 2c37, 2c55, and 3a11 in the liver are shown in FIG. 3-1 and FIG. 3-2.

In the cyp3a (KO/KO)/uPA(+/+)/SCID(+/+) chimeric mice [N2F1] and non-transplanted cyp3a (KO/KO)/uPA(+/+)/ SCID(+/+) mice [N2F1], the expression of mRNA encoding Cyp3a11 that is a representative Cyp3a molecular species in mice was not detected (FIG. 3(f)). When the cyp3a (KO/KO)/ uPA(+/+)/SCID(+/+) chimeric mice [N2F1] were compared with the PXB mice, the expression levels of mRNA encoding Cyp1a2, 2b10, and 2c37 were almost the same between the two (FIGS. 3(a), (b), and (d)), and the expression levels of mRNA encoding Cyp2c29 and 2c55 were higher in the cyp3a (KO/KO)/uPA(+/+)/SCID(+/+) chimeric mice [N2F1] than in the PXB mice (FIGS. 3-1(c) and FIG. 3-2(e)). Moreover, when the cyp3a (KO/KO)/uPA(+/+)/SCID(+/+) chimeric mice [N2F1] were compared with the non-transplanted cyp3a (KO/KO)/uPA(+/+)/SCID(+/+) mice [N2F1], the non-transplanted cyp3a (KO/KO)/uPA(+/+)/SCID(+/+) mice [N2F1] exhibited higher expression levels of mRNA encoding Cyp1a2, 2b10, 2c29, 2c37, and 2c55 than those of the other mice (FIGS. 3(a)-(d) and FIG. 3-2(e)).

Example 4

RT-PCR Analysis of Mouse Cyp mRNA Expression in the Small Intestine

The expression levels of mRNA encoding various mouse CYPs in the small intestine of the cyp3a (KO/KO)/uPA(+/+)/ SCID(+/+) chimeric mice [N2F1], the PXB mice, and the non-transplanted cyp3a(KO/KO)/uPA(+/+)/SCID(+/+) mice [N2F1] prepared in Example 2 above were measured by an RT-PCR method.

The results of analyzing the expression levels of mRNA encoding mouse Cyp2b10, 2c55, and 3a11 in the small intestine are shown in FIG. 4.

In the cyp3a (KO/KO)/uPA(+/+)/SCID(+/+) chimeric mice [N2F1] and the non-transplanted cyp3a (KO/KO)/uPA(+/+)/ SCID(+/+) mice [N2F1], the expression of mRNA encoding Cyp3a11 that is a representative Cyp3a molecular species in mice was not detected (FIG. 4(c)). Moreover, when the cyp3a (KO/KO)/uPA(+/+)/SCID(+/+) chimeric mice [N2F1] were compared with the non-transplanted cyp3a (KO/KO)/uPA (+/+)/SCID(+/+) mice [N2F1], the non-transplanted cyp3a (KO/KO)/uPA(+/+)/SCID(+/+) mice [N2F1] exhibited higher expression levels of mRNA encoding Cyp2b10 and 2c55 than those of the other mice (FIGS. 4(a) and (b)).

Example 5

Mouse Cyp3a Expression Analysis in the Liver by Immunostaining

Frozen sections of the left lateral lobe of the cyp3a (KO/ KO)/uPA(+/+)/SCID(+/+) chimeric mice [N2F1] and PXB mice prepared in Example 2 above were prepared. Immunostaining of the liver was performed using a human specific cytokeratin 8/18 (hCK8/18) antibody (PROGEN) and a mouse Cyp3a antibody (SANTA CRUZ).

The results are shown in FIG. 5.

In the liver of the PXB mice, positive immunostaining was observed for mouse Cyp3a, which is consistent with hCK8/ 18-negative mouse hepatocytes (FIGS. 5A-5C). On the other hand, in the cyp3a (KO/KO)/uPA(+/+)/SCID(+/+) chimeric mice [N2F1], hCK8/18-negative mouse hepatocytes were negative for mouse Cyp3a (FIGS. 5D-5F).

Example 6

Mouse Cyp3a Expression Analysis in the Small Intestine by Immunostaining

Frozen sections of the small intestine of the cyp3a (KO/KO)/uPA(+/+)/SCID(+/+) chimeric mice [N2F1] and the PXB mice prepared in Example 2 above were prepared. Immunostaining of the small intestine was performed using a mouse Cyp3a antibody.

The results are shown in FIG. 6.

In the small intestine of the PXB mice, positive immunostaining was observed for mouse Cyp3a in small intestinal epithelium (FIGS. 6A-6C). On the other hand, in the cyp3a (KO/KO)/uPA(+/+)/SCID(+/+) chimeric mice [N2F1], negative immunostaining was observed for mouse Cyp3a (FIGS. 6D-6F).

Example 7

Midazolam (MDZ) Metabolic Activity in the Liver and the Small Intestine

MDZ metabolic activity was determined using microsomes from the liver and the small intestine from each mouse prepared in Example 2 above. In an experiment using hepatic microsomes, MDZ with a final concentration of 50 umol/L was incubated in hepatic microsomes with a final concentration of 0.1 mg/mL at 37° C. for 5 minutes. In an experiment using small intestinal microsomes, MDZ with a final concentration of 50 umol/L was incubated in small intestinal microsomes with a final concentration of 0.5 mg/mL at 37° C. for 10 minutes. 1'- and 4-hydroxylated metabolites of MDZ were measured using LC-MS/MS.

The results are shown in FIG. 7.

When the cyp3a (KO/KO)/uPA(+/+)/SCID(+/+) chimeric mice [N2F1] were compared with the PXB mice, MDZ metabolic activity in hepatic microsomes was almost the same between the two (FIG. 7 (a)). Meanwhile, regarding MDZ metabolic activity in the small intestinal microsomes, the cyp3a (KO/KO)/uPA(+/+)/SCID(+/+) chimeric mice [N2F1] exhibited MDZ metabolic activity lower than that of the PXB mice, but was almost the same as that of the non-transplanted cyp3a (KO/KO)/uPA(+/+)/SCID(+/+) mice [N2F1] (FIG. 7(b)). It was demonstrated that in the cyp3a (KO/KO)/uPA (+/+)/SCID(+/+) chimeric mice, metabolism by mouse Cyp3a in the small intestine was suppressed than in the PXB mice.

Example 8

Human Hepatocyte Transplantation 2

Human hepatocytes were prepared in a manner similar to that in Example 2 above, and then $5.0 \times 10^5$ human hepatocytes were transplanted into eight cyp3a (KO/KO)/uPA(+/+)/SCID(+/+) mice [N4F1] (2- to 4-week old) obtained in Example 1, in a manner similar to that in Example 2 above.

Figure 8:
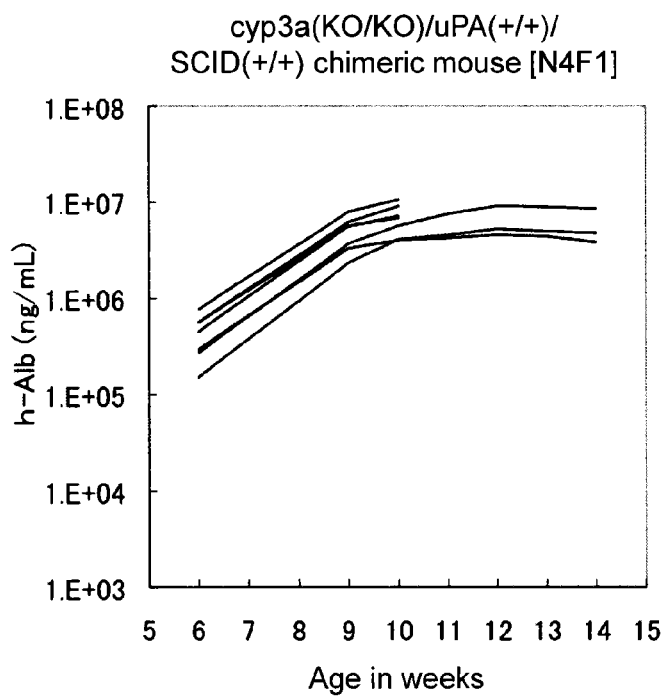
Figure 1:
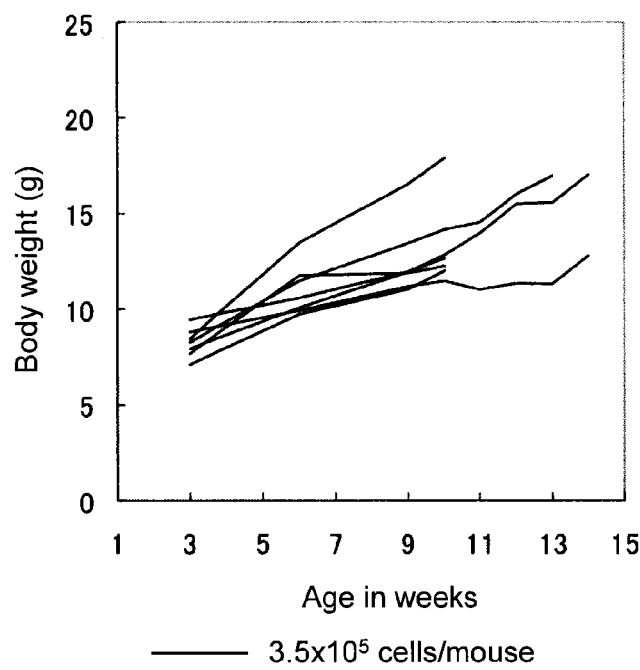
FIG. 1 shows blood human albumin (h-Alb) concentrations (a) and body weights (b) of cyp3a (KO/KO)/uPA(+/+)/SCID(+/+) chimeric mice [N2F1] and PXB mice.
Figures 2, 8:
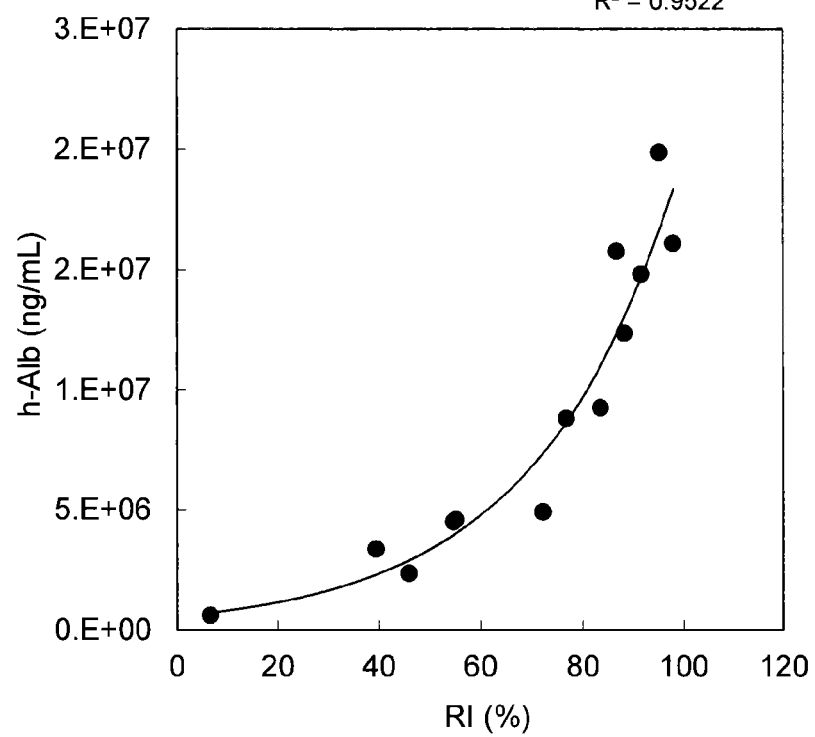

Blood (2 uL each) was collected from the mouse tail vein on weeks 3 and 6 and every week after transplantation and then added to 200 uL of LX-Buffer. Human albumin concentration in mouse blood was measured by immunonephelometry using an autoanalyzer JEOL BM6050 (JEOL Ltd.). As a result, increases in human albumin concentration were observed and five mice were confirmed to have a human albumin concentration of >7 mg/ml (FIG. 8-1(a)). The following experiment was performed using four chimeric mice (two male and two female mice) of these mice. Smooth body weight gain was observed for these mice (FIG. 8-1(b)).

It was considered based on the human albumin concentrations in mouse blood that the engraftment and replacement rates of human hepatocytes that had been transplanted into the cyp3a (KO/KO)/uPA(+/+)/SCID(+/+) mice [N4F1] were higher than those of the human hepatocytes transplanted into the cyp3a (KO/KO)/uPA(+/+)/SCID(+/+) mice [N2F1]. As described above, through back-crossing of the thus obtained mice with uPA(+/+)/SCID(+/+) mice, increases in the engraftment and replacement rates of human hepatocytes were observed.

The cyp3a (KO/KO)/uPA(+/+)/SCID(+/+) chimeric mice [N4F1] were dissected on week 11 or 14, and then frozen sections of each liver lobe were prepared. Frozen sections were stained with an hCK8/18 antibody, and then the hCK8/18 antibody-positive area per mouse liver section was found, thereby allowing the rate of replacement [RI(%)] with human hepatocytes to be determined. The human albumin concentration in the mouse blood and the rates of replacement at the time of dissection were plotted, indicating a correlation similar to that for the PXB mice (FIG. 8-2(c)).

Example 9

Metabolic Studies for Nefazodone Hydrochloride

Eight (8) mg of free/mL nefazodone hydrochloride suspended in 0.5% methylcellulose (resulting in a dose of 10 mg free/kg b.w.) was forcibly administered perorally twice in a volume of 5 mL/kg b.w. at each instance to four (two male and two female mice) cyp3a (KO/KO)/uPA(+/+)/SCID(+/+) mice [N4F1] (week 8 after transplantation (11-week-old)) obtained in Example 8 above by transplantation of human hepatocytes.

Immediately after the first peroral administration of nefazodone hydrochloride, the animals were housed in metabolic cages. Urine was sampled at a time 0 to 8 hours after administration and at a time 8 to 24 hours after administration, at room temperature. After the sampling of urine, the $2^{nd}$ peroral administration of nefazodone hydrochloride was performed. One (1) hour after administration, blood, small intestine, and liver samples were collected. Immediately after blood collection, centrifugation (1000×g, 4° C. for 10 minutes) was performed to prepare blood plasma. Immediately after collection, urine and blood plasma were stored at −80° C. The PXB mice and the SCID(+/+) mice were similarly treated, and thus blood plasma and urine samples were obtained.

Acetonitrile was added to the thus obtained blood plasma and urine, in an amount equivalent thereto, for deproteinization. Centrifugal filtration (Ultrafree-MC centrifugal filtration tube; 0.45 μm, 9500×g, 2 min, 4° C.) was then performed. The thus obtained filtrates were designated as analytical samples.

As a result of analyzing the above samples, unchanged nefazodone was not detected, but Triazoledione metabolite alone was detected in blood plasma of the PXB mice and the SCID(+/+) mice. On the other hand, human-type metabolites, OH-NEF and p-OH-NEF (Mayol R F et al., Drug Metab Dispos 22(2): 304-11, 1994), were detected in addition to unchanged nefazodone and Triazoledione metabolite in blood plasma of the cyp3a (KO/KO)/uPA(+/+)/SCID(+/+) chimeric mice [N4F1] (FIG. 9-1(a)).

Figures 1, 9:
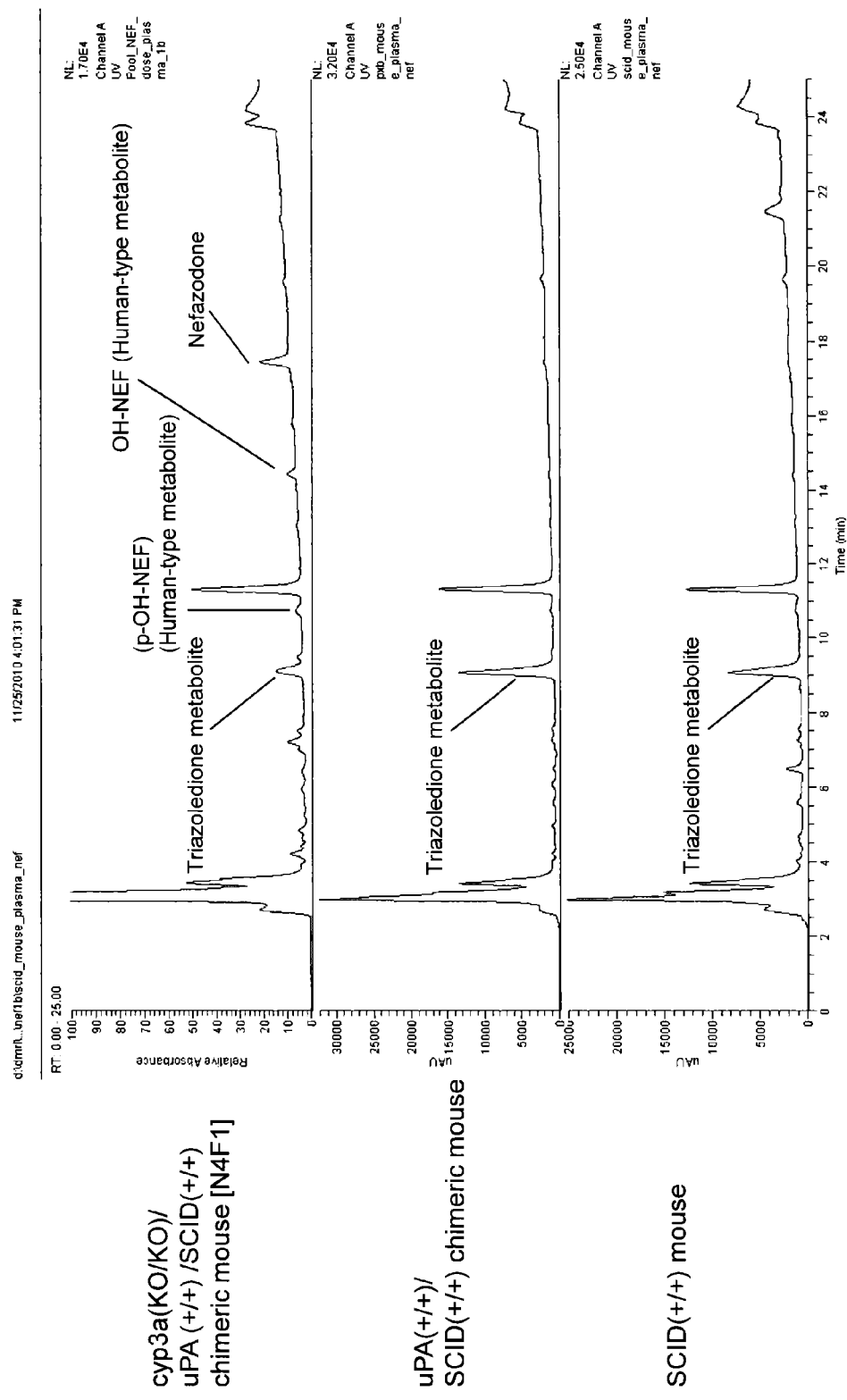
Figures 2, 9:
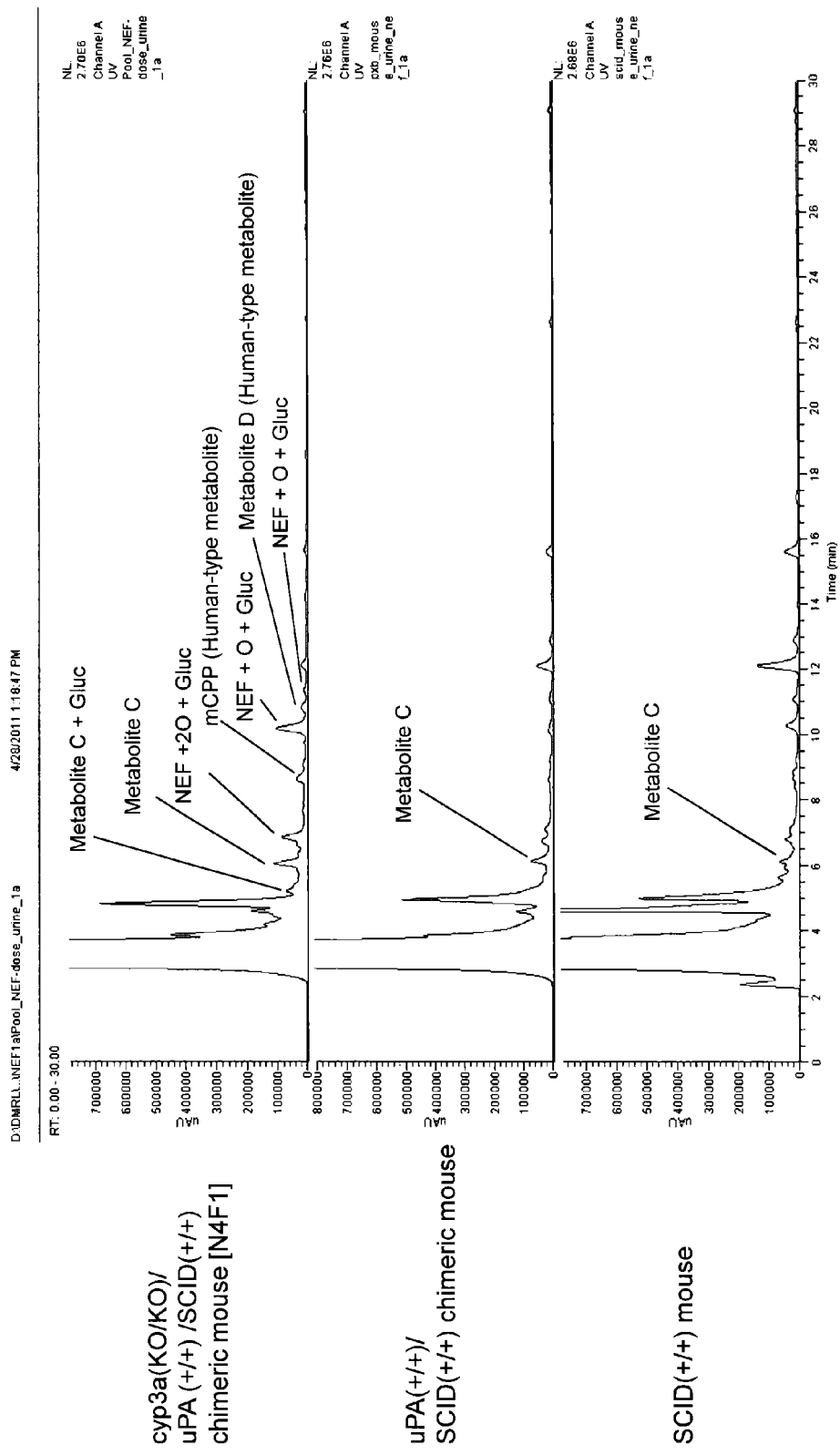

Furthermore, while metabolite C alone was detected as a metabolite in the urine of the PXB mice and the SCID(+/+) mice, 6 types of metabolite, including 2 types of human-type metabolite (mCPP and metabolite D) (Mayol R F et al., Drug Metab Dispos 22(2): 304-11, 1994) were detected in addition to metabolite C in the urine of the cyp3a (KO/KO)/uPA(+/+)/SCID(+/+) chimeric mice [N4F1] (FIG. 9-2(b)).

As shown in the results of the Examples above, in the liver and the small intestine of the cyp3a (KO/KO)/uPA(+/+)/SCID(+/+) chimeric mice, increases in the expression levels of various mouse Cyp(s) were suppressed, in addition to the lack of the expression of mouse Cyp3a. Meanwhile, it was revealed that transplanted human hepatocytes had engrafted into and grown in the liver to express various human CYPs. These results indicate that the cyp3a (KO/KO)/uPA(+/+)/SCID(+/+) chimeric mice had a human metabolic system based on human hepatocytes, in which the endogenous hepatic metabolism and the gastrointestinal metabolism driven by mouse cells were significantly suppressed or deleted. In fact, it was revealed that the metabolic profiles for nefazodone hydrochloride of the cyp3a (KO/KO)/uPA(+/+)/SCID(+/+) chimeric mice reflected the human drug-metabolizing system, unlike the cases of PXB mice and the SCID (+/+) mice. Therefore, it was demonstrated that the cyp3a (KO/KO)/uPA(+/+)/SCID(+/+) chimeric mice are useful as model animals for prediction of human in vivo pharmacokinetics.

INDUSTRIAL APPLICABILITY

According to the present invention, a chimeric non-human animal having an in vivo human hepatocyte population, in which the effects of endogenous non-human animal cells on the drug metabolism are suppressed or deleted, can be provided. In the chimeric non-human animal, the effects of non-human animal cells on the drug metabolism in the liver and the small intestine are suppressed or deleted, and thus the conditions of the drug metabolism in the human liver can be accurately evaluated. Therefore, the chimeric non-human animal in the present invention can be used as an experimental model for human drug metabolism studies, toxicity studies, or the like and it is expected to contribute to fields including drug development and the like.

All publications, patents, and patent applications cited herein are incorporated herein by reference in their entirety.

The invention claimed is:

1. A method for producing a chimeric mouse, comprising transplanting a human hepatocyte into a mouse, the mouse (i) being immunodeficient, (ii) having liver damage, and (iii) lacking functions of an endogenous Cyp3a gene,
wherein the chimeric mouse lacks a drug-metabolizing system from the mouse and is provided with a drug-metabolizing system driven by human hepatocytes.

2. The method according to claim 1, wherein the mouse into which a human hepatocyte is to be transplanted is obtained by a method comprising performing three-way crossing of a mouse or offspring thereof having genetic immunodeficiency, a mouse or offspring thereof genetically having liver damage, and a mouse or offspring thereof genetically lacking the functions of the endogenous Cyp3a gene.

3. The method according to claim 1, wherein the mouse into which a human hepatocyte is to be transplanted is obtained by a method comprising crossing a mouse or offspring thereof having genetic immunodeficiency and genetically having liver damage with a mouse or offspring thereof genetically lacking the functions of the endogenous Cyp3a gene.

4. The method according to claim 1, wherein the mouse into which a human hepatocyte is to be transplanted is obtained by a method comprising crossing a uPA(+/+)/SCID (+/+) mouse with a cyp3a (KO/KO) mouse, and screening for an animal that homozygously has each genetic component.

5. The method according to claim 1, wherein the mouse into which a human hepatocyte is to be transplanted is a cyp3a(KO/KO)/uPA(+/+)/SCID(+/+) mouse.

6. A chimeric mouse, obtained by the method according to claim 1.

7. A chimeric mouse, comprising in vivo human hepatocytes, wherein the chimeric mouse lacks functions of the endogenous Cyp3a gene, and carries the in vivo human hepatocytes.

8. The chimeric mouse according to claim 7, wherein the non-human animal lacks a drug-metabolizing system and is provided with a drug-metabolizing system driven by human hepatocytes.

9. A method of conducting a toxicity study on a test substance, comprising:
administering a test substance to the chimeric mouse according to claim 6; and
evaluating the effects of the test substance on the human hepatocytes.

10. A method for testing a capacity of human hepatocytes to metabolize a test substance, comprising:
administering a test substance to the chimeric mouse according to claim 6; and
evaluating the capacity of human hepatocytes to metabolize the test substance.

11. A method of conducting a toxicity study on a test substance, comprising:
administering a test substance to the chimeric mouse according to claim 7; and
evaluating the effects of the test substance on the human hepatocytes.

12. A method for testing a capacity of human hepatocytes to metabolize a test substance, comprising:
administering a test substance to the chimeric mouse according to claim 7; and
evaluating the capacity of human hepatocytes to metabolize the test substance.

* * * * *